United States Patent [19]

Irie et al.

[11] Patent Number: 4,719,296

[45] Date of Patent: Jan. 12, 1988

[54] SPIROXAZINE COMPOUNDS

[75] Inventors: Masahiro Irie, Osaka; Shuichi Maeda, Saitama, both of Japan

[73] Assignee: Mitsubishi Chemical Industries Limited, Tokyo, Japan

[21] Appl. No.: 822,449

[22] Filed: Jan. 27, 1986

[30] Foreign Application Priority Data

Jan. 25, 1985 [JP]  Japan ................................. 60-12191

[51] Int. Cl.⁴ .................. C07D 413/02; C07D 417/02
[52] U.S. Cl. .......................................... 544/71; 544/6
[58] Field of Search ....................................... 544/6, 71

[56] References Cited

U.S. PATENT DOCUMENTS 4,634,767  1/1987  Hoelscher et al. ............... 544/71 X

*Primary Examiner*—Richard L. Raymond
*Attorney, Agent, or Firm*—Sughrue, Mion, Zinn, Macpeak & Seas

[57] ABSTRACT

A spiroxazine compound represented by the formula:

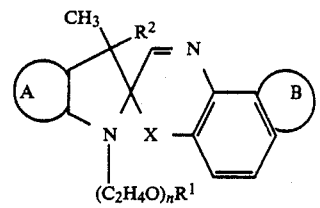

wherein $R^1$ and $R^2$ each represents an alkyl group, an allyl group, an aryl group or an aralkyl group; rings A and B each represents a substituted or unsubstituted benzene ring, a substituted or unsubstituted naphthalene ring or a substituted or unsubstituted heterocyclic ring; X represents an oxygen atom or a sulfur atom; and n represents an integer of from 1 to 6, and a photochromic composition containing said spiroxazine compound are disclosed. The compound is excellent in compatibility to and solubility in high molecular weight compounds, and the composition containing the same stably develops a color of high density upon irradiation of ultraviolet rays.

16 Claims, No Drawings

SPIROXAZINE COMPOUNDS

FIELD OF THE INVENTION

This invention relates to a novel spiroxazine compound and a photochromic composition containing the same. More particularly, it relates to a novel spiroxazine compound having photochromic properties and a composition containing the same which are useful in various recording and memory materials, copying materials, photosensitive materials for printing plates, photosensitive materials for laser beams, photosensitive materials for photo-composition, optical filters, masking materials, actinometers, display devices, and the like.

BACKGROUND OF THE INVENTION

It has hitherto been known that spiroxazine compounds have properties to develop colors or lose their colors upon irradiation of light, i.e., the so-called photochromism, and various photochromic photosensitive materials utilizing these compounds have been proposed. For example, Japanese Patent Application (OPI) No. 36284/80 (the term "OPI" herein used means "published unexamined application") which corresponds to U.S. Pat. No. 4,215,010 and 4,342,668, and U.S. Pat. No. 4,342,663 disclose spironaphthoxazine compounds as photochromic compounds. Japanese Patent Publication No. 28892/70 which corresponds to U.S. Pat. No. 3,578,602 discloses photochromic materials containing spironaphthoxazine compounds. Further, Japanese Patent Publication No. 48631/74 which corresponds to U.S. Pat. No. 3,562,172 and Japanese Patent Application (OPI) No. 112880/85 which corresponds to U.S. patent applications Ser. Nos. 548,660, now abandoned, and 635,696, now U.S. Pat. No. 4,637,698, describe photochromic photosensitive materials comprising a high molecular weight substance having dispersed therein a spiroxazine compound.

In general, photochromic photosensitive materials are obtained by dispersing these spiroxazine compounds in a high molecular weight compound and forming the dispersion into a film.

SUMMARY OF THE INVENTION

An object of this invention is to provide a spiroxazine compound having excellent compatibility to and solubility in high molecular weight compounds and a photochromic composition containing such a compound which provides a photochromic photosensitive material exhibiting high contrast and high color density.

This invention relates to a spiroxazine compound represented by the formula (I):

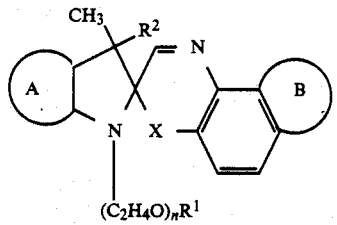

(I)

wherein $R^1$ and $R^2$ each represents an alkyl group, an allyl group, an aryl group or an aralkyl group; rings A and B each represents a substituted or unsubstituted benzene ring, a substituted or unsubstituted naphthalene ring or a substituted or unsubstituted heterocyclic ring; X represents an oxygen atom or a sulfur atom; and n represents an integer of from 1 to 6, and to a photochromic composition containing the spiroxazine compound represented by the formula (I) and a phenolic compound.

DETAILED DESCRIPTION OF THE INVENTION

In the above-described formula (I), the alkyl group as represented by $R^1$ includes a methyl group, an ethyl group and a straight or branched chain alkyl group having from 3 to 28 carbon atoms. The alkyl group as represented by $R^2$ includes a methyl group, an ethyl group and a straight or branched chain alkyl group having from 3 to 6 carbon atoms, preferably a methyl group, an ethyl group and a propyl group, and more preferably a methyl group and an ethyl group.

The aryl group as represented by $R^1$ or $R^2$ includes a phenyl group, a naphthyl group, etc., and preferably a phenyl group. The aralkyl group includes a benzyl group, a phenethyl group, etc.

The spiroxazine compounds represented by the formula (I) according to the present invention preferably include those represented by the following formula (II) or (III):

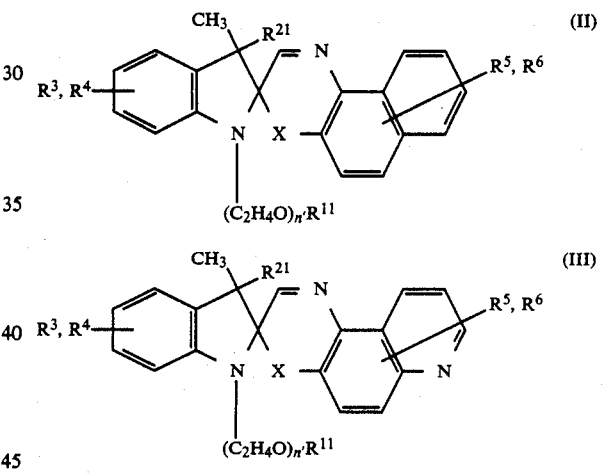

wherein $R^{11}$ and $R^{21}$ each represents an alkyl group; $R^3$, $R^4$, $R^5$ and $R^6$ each represents a hydrogen atom, a halogen atom, an alkyl group, an alkoxy group or an alkoxycarbonyl group; and n' represents an integer of from 1 to 4.

In the formulae (II) and (III), the halogen atom as represented by $R^3$, $R^4$, $R^5$ or $R^6$ includes a chlorine atom, a bromine atom, an iodine atom, etc. The alkyl group as represented by $R^3$, $R^4$, $R^5$ or $R^6$ includes a methyl group, an ethyl group or a straight or branched chain alkyl group having from 3 to 6 carbon atoms, preferably an alkyl group having from 1 to 3 carbon atoms, and most preferably a methyl or an ethyl group. The alkoxy group includes a methoxy group, an ethoxy group and a straight or branched chain alkoxy group having from 3 to 6 carbon atoms, preferably an alkoxyl group having from 1 to 3 carbon atoms, and most preferably a methoxy or an ethoxy group. The alkoxycarbonyl group includes a methoxycarbonyl group, an ethoxycarbonyl group and a straight or branched chain alkoxycarbonyl group having from 3 to 6 carbon atoms, preferably an alkoxycarbonyl group having from 1 to 3 carbon atoms, and most preferably a methoxycarbonyl or an ethoxycarbonyl group.

The spiroxazine compounds according to the present invention can be prepared by reacting, a compound represented by the formula (IV):

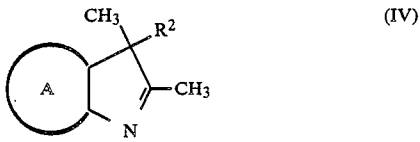

wherein $R^2$ and ring A are as defined above, with a p-toluenesulfonic ester represented by the formula (V):

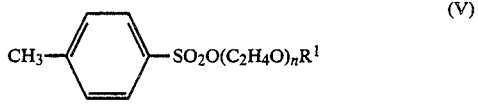

wherein $R^1$ and n are as defined above, and then reacting the resulting compound with a compound represented by the formula (VI):

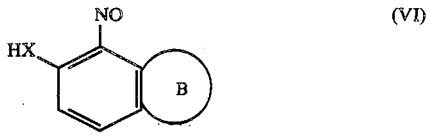

wherein X and ring B are as defined above.

The alkylation reaction with the p-toluenesulfonic ester (V) can be carried out in the absence of a solvent or in the presence of a non-polar solvent, such as aromatic solvents, e.g., chlorobenzene, dichlorobenzene, etc., at a temperature of from 80° C. to 200° C., and preferably in the absence of a solvent at a temperature of from 130° to 150° C.

The reaction of the alkylation reaction product with the compound (VI) can be carried out in a polar or non-polar solvent, such as alcohols, e.g., methanol, ethanol, propanol, butanol, etc., a ketone, e.g., acetone, methyl ethyl ketone, etc., a halogenated hydrocarbon, e.g., dichloromethane, trichloroethane, etc., and the like, in the presence of a basic catalyst, e.g., piperidine, piperazine, morpholine, etc. The reaction temperature ranges from 0° to 200° C. This reaction is preferably performed in ethanol, methyl ethyl ketone or acetone in the presence of piperidine at 40° to 120° C.

The compounds according to the present invention can also be prepared by reacting a compound represented by the formula (VII):

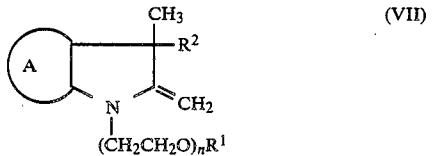

wherein $R^1$, $R^2$, ring A and n are as defined above, with the compound represented by the formula (VI).

The above reaction can usually be carried out in a polar or non-polar solvent, such as alcohols, e.g., methanol, ethanol, propanol, butanol, etc., ketones, e.g., acetone, methyl ethyl ketone, etc., halogenated hydrocarbons, e.g., dichloromethane, trichloroethane, etc. The reaction temperature ranges from 0° to 200° C., and preferably from 40° to 120° C.

The spiroxazine compounds represented by the formula (I) in accordance with the present invention are novel compounds exhibiting photochromism. In other words, they develop a color upon irradiation with ultraviolet rays and turn to colorless by irradiation with visible light or heating to a temperatue of 50° C. or higher. This color appearance and disappearance are reversible.

The compounds according to the present invention are particularly excellent in compatibility to and solubility in high molecular weight compounds. Therefore, they can easily be dissolved in an appropriate binder to provide photochromic compositions which develop deep colors and have excellent preservability sufficient to stably repeat color appearance and disappearance. Such photochromic compositions are useful in various recording and memory materials, copying materials, photosensitive materials for printing plates, photosensitive materials for laser beams, photosensitive materials for photo-composition, optical filters, masking materials, actinometers, display devices, and the like.

Binders which can be used in the present invention include a polyester resin, a polystyrene resin, a polyvinyl butyral resin, polyvinylidene chloride, polyvinyl chloride, polymethyl methacrylate, polyvinyl acetate, cellulose acetate, an epoxy resin, a phenol resin, and the like, with a polyester resin, a polyvinyl butyral resin and a polyvinylidene chloride resin being preferred.

In a preferred embodiment of the present invention, the photochromic composition containing the compound of the formula (I) further contains a phenolic compound to enhance color developability at high temperatures.

The phenolic compound which can be used in the present invention includes, for example, a bisphenol compound represented by the formula (VIII):

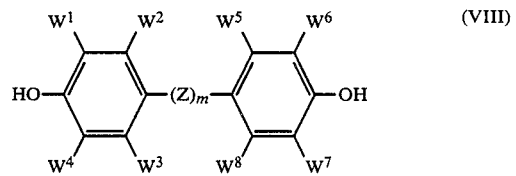

wherein $W^1$, $W^2$, $W^3$, $W^4$, $W^5$, $W^6$, $W^7$ and $W^8$, each represents a hydrogen atom, a halogen atom or an aliphatic hydrocarbon group; Z represents

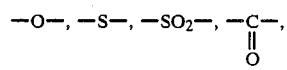

an alkylene group or an alkenylene group; and m represents 0 or 1, and a phenolic compound represented by the formula (IX):

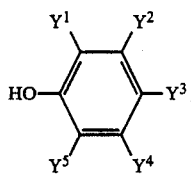

wherein $Y^1$, $Y^2$, $Y^3$, $Y^4$ and $Y^5$ each represents an aliphatic hydrocarbon group, a halogen atom, an alkoxy group, a phenoxy group or a hydroxyl group.

The alkenylene group or alkenylene group as represented by Z or the aliphatic hydrocarbon group as represented by $W^1$, $W^2$, $W^3$, $W^4$, $W^5$, $W^6$, $W^7$ or $W^8$ in the formula (VIII) or the aliphatic hydrocarbon group or alkoxy group as represented by $Y^1$, $Y^2$, $Y^3$, $Y^4$ or $Y^5$ in the formula (IX) preferably contains from 1 to 4 carbon atoms, and more preferably 1 or 2 carbon atoms.

Among these phenolic compounds, the bisphenol compounds of the formula (VIII) are preferred, and the more preferred are shown below.

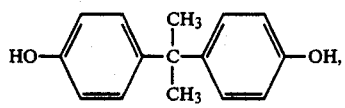

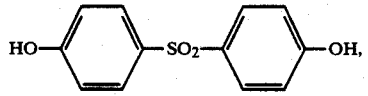

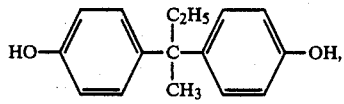

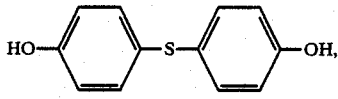

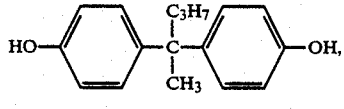

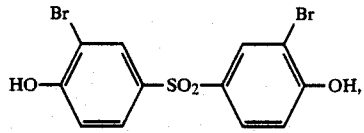

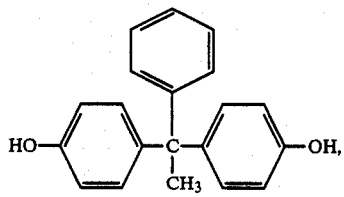

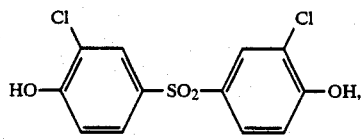

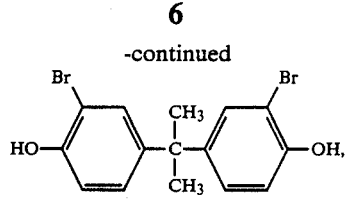

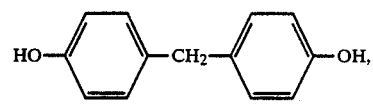

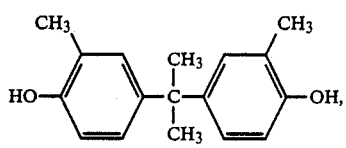

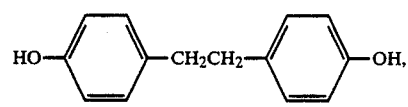

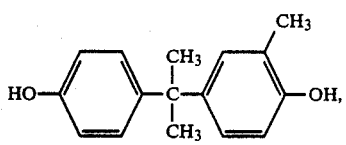

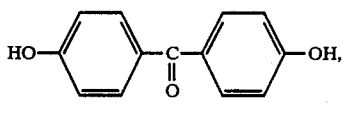

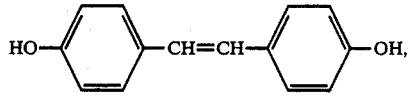

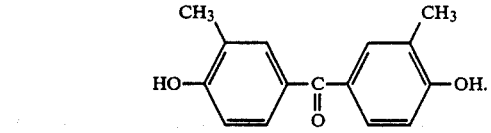

These phenolic compounds are usually used in an amount of from 0.1 to 150% by weight, and preferably from 3 to 50% by weight, based on the spiroxazine compound of the formula (I).

The present invention will now be illustrated in greater detail with reference to the following examples, but it should be understood that the present invention is not deemed to be limited thereto.

EXAMPLE 1

A mixture of 15.9 g of 2,3,3-trimethylindolenine represented by the formula:

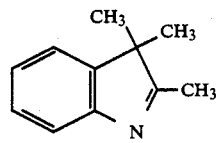

and 23.0 g of methoxyethyl p-toluenesulfonate of the formula:

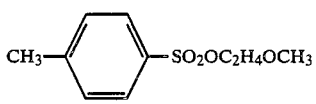

was allowed to react at 140° C. for 3 hours. After cooling to room temperature, 300 ml of methyl ethyl ketone was added to the reaction mixture. A suspension of 18 g of 1-nitroso-2-naphthol of the formula:

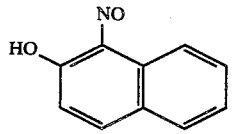

in 100 ml of methyl ethyl ketone and 9 ml of piperidine were added thereto while refluxing, followed by allowing the mixture to react for 1 hour at reflux. After cooling, the reaction mixture was filtered, and the solvent was removed from the filtrate by distillation. The residue was dissolved in 200 ml of acetone, and 400 ml of methanol was added thereto, followed by allowing to stand in a freezer overnight. The precipitated crystals were collected by filtration to obtain 10 g of a crude product, which was then separated and purified by thin layer chromatography (developing solvent:benzene-n-hexane=1:1 by volume) to give a spiroxazine compound represented by the formula:

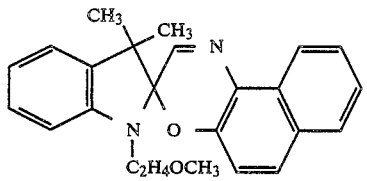

as a colorless crystal having a melting point of 136° to 138° C.

A composition consisting of 4 g of the thus prepared spiroxazine compound, 10 g of a thermoplastic polyester resin (Vylon-200, produced by Toyo Spinning Co., Ltd.) and 100 g of methyl ethyl ketone was coated on a 100 μm thick polyester film (produced by DIAFOIL Co., Ltd.) using a bar coater No. 3 and dried at 75° C. for 10 minutes. The resulting sample was colorless in a usual state but developed a high density blue color ($\lambda_{max}$=606 nm) upon irradiation with ultraviolet rays. When the color-developed sample was irradiated with visible light or heated at 50° C. or higher, it returned to the original colorless state. This color appearance and disappearance could be repeatedly effected.

EXAMPLE 2

In the same manner as described in Example 1 but using 26.2 g of methoxyethoxyethyl p-toluenesulfonate in place of 23.0 g of methoxyethyl p-toluenesulfonate, a spiroxazine compound represented by the formula:

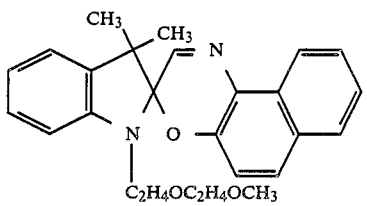

was obtained.

A photochromic composition having the same composition as used in Example 1 but using the thus prepared spiroxazine compound was coated on a polyester film in the same manner as in Example 1. The resulting sample developed a high density blue color ($\lambda_{max}$=606 nm) upon irradiation with ultraviolet rays but returned to the original colorless state by irradiating visible light or heating to 50° C. or higher. This color change could be repeatedly effected.

EXAMPLE 3

In 500 ml of ethanol was dissolved 28.7 g of a compound of the formula:

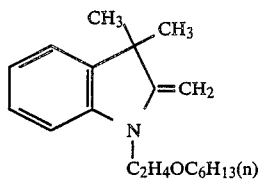

and 17.3 g of a compound of the formula:

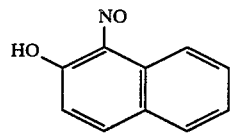

was added to the resulting solution, followed by allowing the mixture to react under reflux for 2 hours. After cooling to room temperature, the solvent was removed by distillation. The residue was subjected to purification by column chromatography using benzene as an eluent to obtain a spiroxazine compound of the formula:

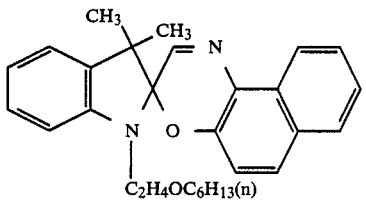

A photochromic composition having the same composition as used in Example 1 but using the thus prepared spiroxazine compound was coated on a polyester film in the same manner as in Example 1. The resulting sample developed a high density blue color ($\lambda_{max}$=606 nm) upon irradiation with ultraviolet rays but returned to the original colorless state upon irradiation with visible light or heating to 50° C. or higher. This color change could be repeatedly effected.

EXAMPLES 4 TO 47

Spiroxazine compounds shown in Table 1 below were synthesized in the same manner as described in Examples 1 to 3. Each of the resulting compounds was coated on a polyester film and irradiated with ultraviolet rays in the same manner as described in Example 1.

The color developed and its maximum absorption wavelength are shown in Table 1.

When the color-developed sample was irradiated with visible light or heated to 50° C. or higher, it returned to the original colorless state. This color change could be repeatedly effected.

TABLE 1

| Example No. | Structure | Color | $\lambda_{max}$ (nm) |
|---|---|---|---|
| 4 | (spiroxazine with N–$C_2H_4OC_2H_4OC_2H_4OCH_3$) | blue | 606 |
| 5 | (spiroxazine with N–$C_2H_4OC_2H_4OC_2H_4OC_2H_4OCH_3$) | blue | 606 |
| 6 | (spiroxazine with N–$C_2H_4OC_2H_5$) | blue | 606 |
| 7 | (spiroxazine with N–$C_2H_4OC_3H_7(n)$) | blue | 606 |
| 8 | (spiroxazine with N–$C_2H_4OC_4H_9(n)$) | blue | 606 |
| 9 | (spiroxazine with N–$C_2H_4OC_5H_{11}(n)$) | blue | 606 |

TABLE 1-continued
| Example No. | Structure | Color | $\lambda_{max}$ (nm) |
|---|---|---|---|
| 10 | 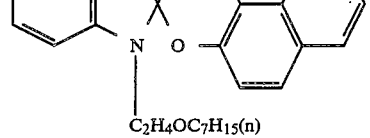 C₂H₄OC₇H₁₅(n) | blue | 606 |
| 11 | 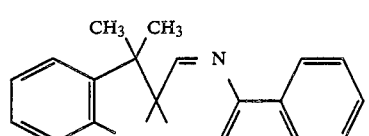 C₂H₄OC₈H₁₇(n) | blue | 606 |
| 12 | 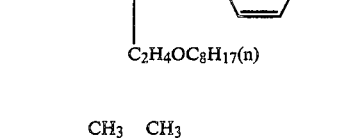 C₂H₄OC₉H₁₉(n) | blue | 606 |
| 13 | 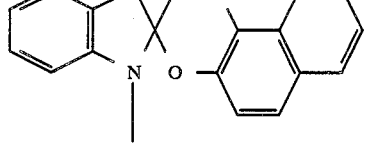 C₂H₄OCH₂CHC₄H₉(n) \| C₂H₅ | blue | 606 |
| 14 | 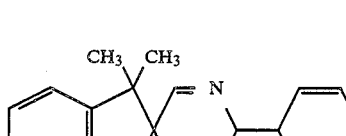 C₂H₄OC₁₀H₂₁(n) | blue | 606 |
| 15 | 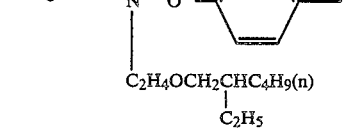 C₂H₄OC₁₆H₃₃(n) | blue | 606 |

TABLE 1-continued
| Example No. | Structure | Color | $\lambda_{max}$ (nm) |
|---|---|---|---|
| 16 | 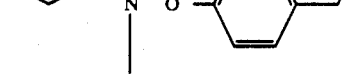  C₂H₄OC₁₈H₃₇(n) | blue | 606 |
| 17 | 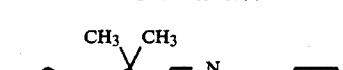  C₂H₄OC₂₀H₄₁(n) | blue | 606 |
| 18 | 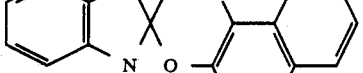  C₂H₄OC₂₈H₅₇(n) | blue | 606 |
| 19 | 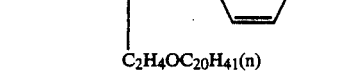  C₂H₄OC₂H₄OC₂H₅ | blue | 606 |
| 20 | 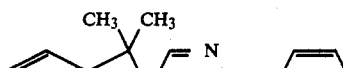  C₂H₄OC₂H₄OC₂H₄OC₂H₅ | blue | 606 |
| 21 | 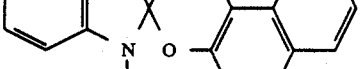  C₂H₄OC₂H₄OC₂H₄OC₂H₄OC₂H₅ | blue | 606 |
| 22 | 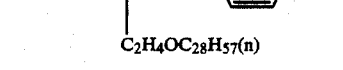  C₂H₄OC₂H₄OC₈H₁₇(n) | blue | 606 |

TABLE 1-continued

| Example No. | Structure | Color | $\lambda_{max}$ (nm) |
|---|---|---|---|
| 23 | (structure with indoline bearing two CH₃ groups, N-C₂H₄OC₃H₇(i), fused to oxazine with 2-naphthyl) | blue | 606 |
| 24 | (5-Cl indoline, two CH₃, N-C₂H₄OCH₃, naphthoxazine) | blue | 604 |
| 25 | (5-Br indoline, two CH₃, N-C₂H₄OCH₃, naphthoxazine) | blue | 604 |
| 26 | (5-I indoline, two CH₃, N-C₂H₄OCH₃, naphthoxazine) | blue | 604 |
| 27 | (5-CH₃ indoline, two CH₃, N-C₂H₄OC₂H₅, naphthoxazine) | blue | 605 |
| 28 | (5-H₃CO indoline, two CH₃, N-C₂H₄OCH₃, naphthoxazine) | blue | 603 |
| 29 | (5,6-di-CH₃ indoline, two CH₃, N-C₂H₄OCH₃, naphthoxazine) | blue | 605 |

TABLE 1-continued

| Example No. | Structure | Color | $\lambda_{max}$ (nm) |
|---|---|---|---|
| 30 | 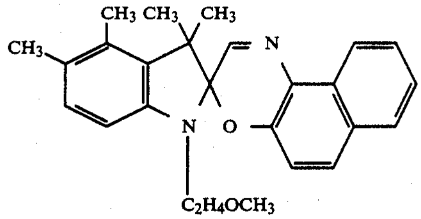 | blue | 605 |
| 31 | 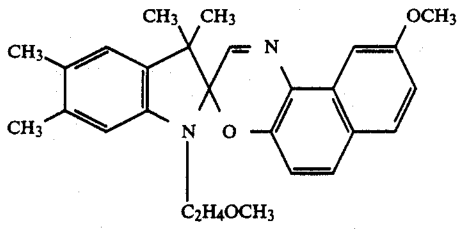 | blue | 606 |
| 32 | 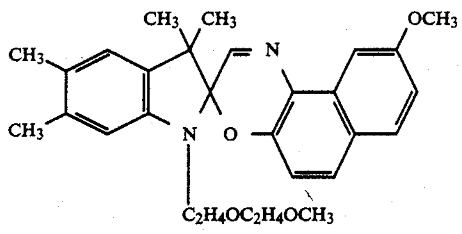 | blue | 606 |
| 33 | 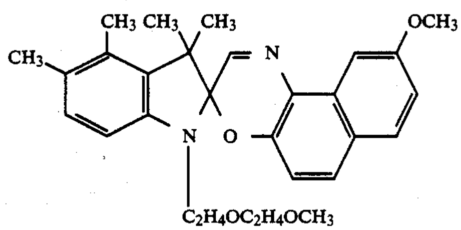 | blue | 606 |
| 34 | 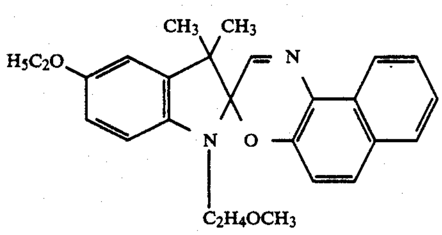 | blue | 603 |
| 35 | 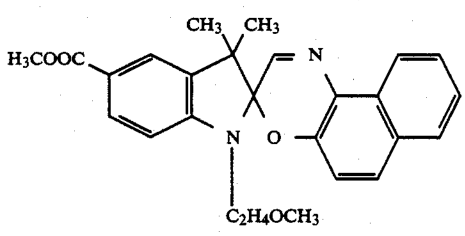 | blue | 607 |
| 36 | 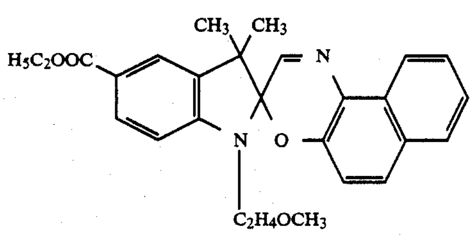 | blue | 607 |

TABLE 1-continued

| Example No. | Structure | Color | $\lambda_{max}$ (nm) |
|---|---|---|---|
| 37 | [indoline with CH3, CH3 at 3-position; N-C2H4OCH3; =N linked to 7-Cl-naphthalene-2-olate] | blue | 606 |
| 38 | [indoline with CH3, CH3; N-C2H4OC2H4OCH3; =N linked to 7-Br-naphthalene-2-olate] | blue | 606 |
| 39 | [indoline with CH3, CH3; N-C2H4OC2H4OCH3; =N linked to 6-Cl-naphthalene-2-olate] | blue | 606 |
| 40 | [indoline with CH3, CH3; N-C2H4OC2H5; =N linked to 6-Br-naphthalene-2-olate] | blue | 606 |
| 41 | [indoline with CH3, CH3; N-C2H4OC4H9(sec); =N linked to 6-I-naphthalene-2-olate] | blue | 606 |
| 42 | [indoline with CH3, CH3; N-C2H4OC2H4OCH3; =N linked to 7-CH3-naphthalene-2-olate] | blue | 606 |
| 43 | [indoline with CH3, CH3; N-C2H4OC2H4OCH3; =N linked to 7-OCH3-naphthalene-2-olate] | blue | 606 |

TABLE 1-continued

| Example No. | Structure | Color | $\lambda_{max}$ (nm) |
|---|---|---|---|
| 44 | [indoline with CH₃, CH₃ substituents; N-C₂H₄OC₂H₄OC₂H₅; spiro to naphthoxazine with OCH₃] | blue | 605 |
| 45 | [indoline with CH₃, CH₃; N-C₂H₄OCH₃; spiro to naphthoxazine with COOCH₃] | blue | 605 |
| 46 | [indoline with CH₃, CH₃; N-C₂H₄OCH₃; spiro to naphthoxazine with two CH₃ groups] | blue | 606 |
| 47 | [indoline with CH₃, CH₃; N-C₂H₄OCH₃; spiro to naphthoxazine with two CH₃ groups] | blue | 606 |

COMPARATIVE EXAMPLE 1

A photochromic composition having the same composition as in Example 1 but using the comparative spiroxazine compound shown in Table 2 below in an amount of 20% by weight, 30% by weight or 40% by weight based on the polyester resin was coated on a polyester film in the same manner as in Example 1. Each of the resulting samples was irradiated with ultraviolet rays, and the color density developed was determined.

The spiroxazine compounds obtained in Examples 1 and 2 were also tested in the same manner as described above, and the results obtained are shown in Table 2 as relative values taking the color density of the comparative sample as 100.

TABLE 2

| Compound Used | Structure | Color Density 20%* | 30%* | 40%* |
|---|---|---|---|---|
| Comparative compound | [indoline with CH₃, CH₃; N-CH₃; spiro to naphthoxazine] | 100 | 100 | 100 |

TABLE 2-continued

| Compound Used | Structure | Color Density 20%* | 30%* | 40%* |
|---|---|---|---|---|
| Compound of Example 1 | 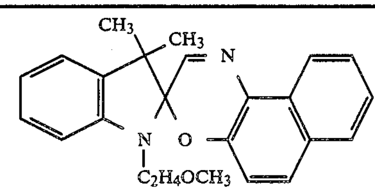 | 130 | 130 | 135 |
| Compound of Example 2 | 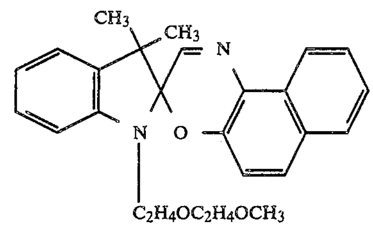 | 140 | 145 | 150 |

Note:
*Percents by weight of the spiroxazine compound based on the polyester resin.

The results of Table 2 prove that the compounds according to the present invention provide photochromic films which develop colors having higher densities as compared with the comparative compound.

EXAMPLE 48

A mixture of 15.9 g of 2,3,3-trimethylindolenine of the formula:

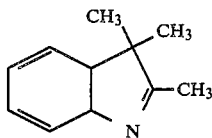

and 23.0 g of methoxyethyl p-toluenesulfonate of the formula:

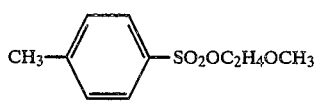

was allowed to react at 140° C. for 3 hours. After cooling to room temperature, 300 ml of methyl ethyl ketone was added to the reaction mixture, followed by refluxing. A suspension of 18.0 g of 5-nitroso-6-quinolinol of the formula:

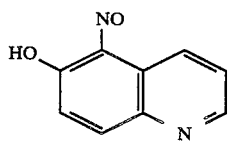

in 100 ml of methyl ethyl ketone and 9 ml of piperidine were added thereto while refluxing, and the resulting mixture was allowed to react for 1 hour at reflux. After cooling, the reaction mixture was extracted with chloroform-water, and the extract was dried. The solvent was removed by distillation, and the residue was purified by column chromatography on silica gel using benzene as an eluent to yield 9.3 g of pale yellow crystals of a spiroxazine compound of the formula:

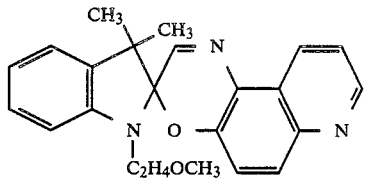

A composition consisting of 4 g of the thus prepared spiroxazine compound, 10 g of a thermoplastic polyester resin (Vylon-200, produced by Toyo Spinning Co., Ltd.) and 100 g of methyl ethyl ketone was coated on a 100 $\mu$m thick polyester film (produced by DIAFOIL Co., Ltd.) using a bar coater No. 3 and dried at 75° C. for 10 minutes. The resulting sample was pale yellow-colored in a usual state but developed a high density blue color ($\mu_{max}=620$ nm) upon irradiation with ultraviolet rays. When color-developed sample was irradiated with visible light or heated at 50° C. or higher, it returned to its original hue. This color change could be repeatedly effected.

EXAMPLE 49

In the same manner as described in Example 48 but using 26.2 g of methoxyethoxyethyl p-toluenesulfonate in place of 23.0 g of methoxyethyl p-toluenesulfonate, a spiroxazine compound of the formula:

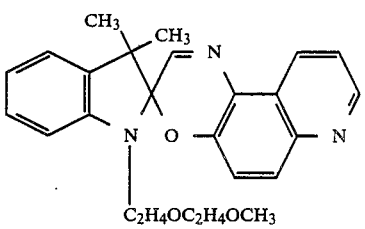

was obtained.

The thus obtained spiroxazine compound was coated on a polyester film in the same manner as in Example 48. The resulting sample developed a deep blue color ($\lambda_{max}$=620 nm) upon irradiation of ultraviolet rays and returned to the original colorless state upon irradiation of visible light or heating to 50° C. or higher. This color change could be repeatedly effected.

EXAMPLE 50

In 500 ml of ethanol was dissolved 24.5 g of a compound of the formula:

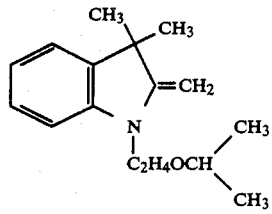

and 18.0 g of a compound of the formula:

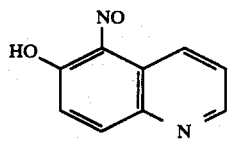

was added to the solution, followed by allowing the mixture to react at reflux for 2 hours. After cooling to room temperature, the solvent was removed by distillation, and the residue was purified by column chromatography using benzene as an eluent to obtain a spiroxazine compound of the formula:

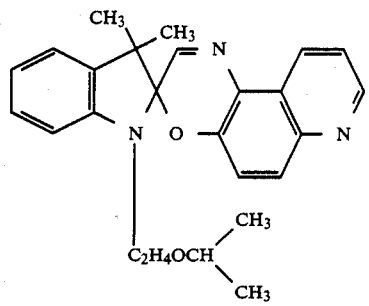

The thus obtained spiroxazine compound was coated on a polyester film in the same manner as in Example 48. The resulting sample developed a deep blue color ($\lambda_{max}$=620 nm) upon irradiation of ultraviolet rays and returned to the original colorless state upon irradiation of visible light or heating to 50° C. or higher. This color change could repeatedly be effected.

EXAMPLES 51 TO 74

Spiroxazine compounds shown in Table 3 below were synthesized in the same manner as described in Examples 48 to 50. Each of the resulting compounds was coated on a polyester film and irradiated with ultraviolet rays in the same manner as described in Examples 48. The color developed and its maximum absorption wavelength are shown in Table 3.

When the color-developed sample was irradiated with visible light or heated to 50° C. or higher, it returned to the original colorless state. This color change could be repeatedly effected.

| Example No. | Structure | Color | $\lambda_{max}$ (nm) |
|---|---|---|---|
| 51 | [structure with C₂H₄OC₂H₄OC₂H₄OCH₃ substituent] | blue | 620 |
| 52 | [structure with C₂H₄OC₂H₄OC₂H₄OC₂H₄OCH₃ substituent] | " | " |
| 53 | [structure with C₂H₄OC₂H₅ substituent] | " | " |

-continued

| Example No. | Structure | Color | $\lambda_{max}$ (nm) |
|---|---|---|---|
| 54 | (structure with C₂H₄OC₃H₇(n) substituent) | " | " |
| 55 | (structure with C₂H₄OC₄H₉(n) substituent) | " | " |
| 56 | (structure with C₂H₄OC₄H₉(sec) substituent) | " | " |
| 57 | (structure with C₂H₄OC₆H₁₃(n) substituent) | " | " |
| 58 | (structure with C₂H₄OC₈H₁₇(n) substituent) | " | " |
| 59 | (structure with C₂H₄OCH₂CHC₄H₉(n) substituent, with C₂H₅ branch) | " | " |

-continued

| Example No. | Structure | Color | λ_max (nm) |
|---|---|---|---|
| 60 | (structure with C₂H₄OC₁₆H₃₃(n) substituent) | " | " |
| 61 | (structure with C₂H₄OC₂H₄OC₂H₅ substituent) | " | " |
| 62 | (structure with C₂H₄OC₂H₄OC₄H₉(n) substituent) | " | " |
| 63 | (structure with C₂H₄OCH₂CH=CH₂ substituent) | " | " |
| 64 | (Cl-substituted structure with C₂H₄OCH₃ substituent) | " | 625 |
| 65 | (structure with C₂H₅ and C₂H₄OCH₃ substituents) | " | 620 |

-continued

| Example No. | Structure | Color | λ_max (nm) |
|---|---|---|---|
| 66 | (structure) | " | " |
| 67 | (structure) | " | 625 |
| 68 | (structure) | " | 620 |
| 69 | (structure) | " | 625 |
| 70 | (structure) | " | " |
| 71 | (structure) | " | " |

| Example No. | Structure | Color | λ_max (nm) |
|---|---|---|---|
| 72 | (structure with H5C2O, OCH3, C2H4OCH3) | " | " |
| 73 | (structure with H3COOC, CH3, C2H4OCH3) | " | " |
| 74 | (structure with Cl, C2H4OCH3) | " | 620 |

EXAMPLES 75 TO 79

Spiroxazine compounds shown in Table 4 below were synthesized in accordance with the process described in Examples 1 to 3 and 48 to 50. Each of the resulting compounds was coated on a polyester film and irradiated with ultraviolet rays in the same manner as in Example 1. The color developed and its maximum absorption wavelength are shown in Table 4.

When the color-developed sample was irradiated with visible light or heated to 50° C. or higher, it returned to the original colorless state. This color change could repeatedly be effected.

TABLE 4

| Example No. | Structure | Color | λ_max (nm) |
|---|---|---|---|
| 75 | (structure with S, C2H4OCH3, naphthalene) | green | 705 |
| 76 | (structure with S, C2H4OCH3) | " | 720 |
| 77 | (structure with N, O, C2H4OCH3) | blue | 625 |
| 78 | (structure with O, C2H4OCH3, isoquinoline) | " | 610 |

TABLE 4-continued

| Example No. | Structure | Color | $\lambda_{max}$ (nm) |
|---|---|---|---|
| 79 | [structure: CH3, CH3, pyridine-indoline with N-C2H4OCH3, spiro-O-naphthalene] | " | 615 |

COMPARATIVE EXAMPLE 2

A photochromic composition having the same composition as in Example 48 but using each of the compounds shown in Table 5 as a spiroxazine compound in an amount of 20% by weight, 30% by weight or 40% by weight based on the polyester resin was coated on a polyester film in the same manner as in Example 48. Each of the resulting samples was irradiated with ultraviolet rays, and the color density developed was determined. The results obtained are shown in Table 5 taking the color density of the comparative sample as 100.

TABLE 5

| Compound Used | Structure | Color Density 20%* | 30%* | 40%* |
|---|---|---|---|---|
| Comparative compound | [structure with N-CH3] | 100 | 100 | 100 |
| Compound of Example 48 | [structure with N-C2H4OCH3] | 130 | 135 | 135 |
| Compound of Example 49 | [structure with N-C2H4OC2H4OCH3] | 140 | 140 | 145 |

*Note:
Percents by weight of the spiroxazine compound based on the polyester resin.

The results of Table 5 above prove that the compounds according to the present invention provide photochromic films which develop colors having higher densities as compared with the comparative compound.

EXAMPLE 80

A composition consisting of 4 g of the spiroxazine compound obtained in Example 1, 0.4 g of bisphenol A, 14 g of a copolymer of polyvinylchloride-vinylidene chloride (#1000, manufactured by Denki Kagaku Kogyo Co., Ltd.) and 100 g of a mixed solvent of toluene, tetrahydrofuran and cyclohexane (2:2:1 by volume) was coated on a 100 μm thick polyester film (produced by DIAFOIL Co., Ltd.) using a bar coater No. 3, and dried at 75° C. for 10 minutes. The resulting sample was colorless in a usual state but developed a high density blue color ($\lambda_{max}$=618 nm) with satisfactory color development stability upon irradiation with ultraviolet rays. Color developability at high temperatures was also satisfactory.

When the color-developed sample was irradiated with visible light, it returned to the original colorless state. This color change could be repeatedly effected.

EXAMPLE 81

The same composition as used in Example 80 but containing 0.4 g of bisphenol S of the formula:

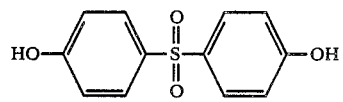

in place of bisphenol A was coated on a polyester film in the same manner as in Example 80. The resulting sample developed a deep blue color ($\lambda_{max}$=617 nm) upon irradiation of ultraviolet rays and returned to the original colorless state upon irradiation of visible light. This color change could repeatedly be effected.

EXAMPLES 82 TO 93

The same composition as used in Example 80 but using a spiroxazine compound and a phenolic compound shown in Table 6 below was coated on a polyester film in the same manner as in Example 80, and the resulting sample was irradiated with ultraviolet rays. The color developed and its maximum absorption wavelength are shown in Table 6.

When the color-developed sample was irradaited with visible light, it returned to the original colorless state. This color change could repeatedly be effected.

TABLE 6

| Example No. | Spiroxazine Compound | Phenolic Compound | Color | $\lambda_{max}$ (nm) |
|---|---|---|---|---|
| 82 | Compound of Example 1 | HO-C6H4-C(C2H5)(CH3)-C6H4-OH | blue | 618 |
| 83 | Compound of Example 1 | HO-C6H4-C(C3H7(n))(CH3)-C6H4-OH | " | " |
| 84 | Compound of Example 1 | HO-C6H4-C(C6H5)(CH3)-C6H4-OH | " | " |
| 85 | Compound of Example 1 | HO-(3-CH3-C6H3)-C(CH3)(CH3)-(3-CH3-C6H3)-OH | " | " |
| 86 | Compound of Example 1 | HO-(3-Br-C6H3)-C(CH3)(CH3)-(3-Br-C6H3)-OH | " | " |
| 87 | Compound of Example 1 | HO-C6H4-CH=CH-C6H4-OH | " | " |
| 88 | Compound of Example 1 | HO-C6H4-S-C6H4-OH | " | " |
| 89 | Compound of Example 1 | HO-C6H4-CH2-C6H4-OH | " | " |
| 90 | Compound of Example 1 | HO-C6H4-C(=O)-C6H4-OH | " | " |
| 91 | Compound of Example 2 | HO-C6H4-C(CH3)(CH3)-C6H4-OH | " | " |
| 92 | Compound of Example 48 | " | greenish blue | 626 |
| 93 | Compound of Example 49 | " | greenish blue | " |

REFERENCE EXAMPLE

The color densities of the colors developed in Examples 1, 80 and 81 are shown in Table 7 below taking that of Example 1 as 100.

TABLE 7

| Example No. | Spiroxazine Compound | Phenolic Compound | Color Density |
|---|---|---|---|
| 1 | 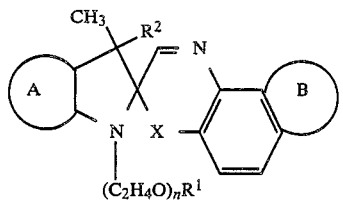 | — | 100 |
| 80 | " | 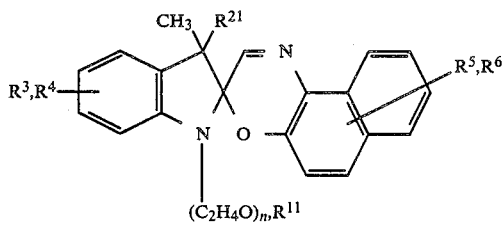 | 156 |
| 81 | " | 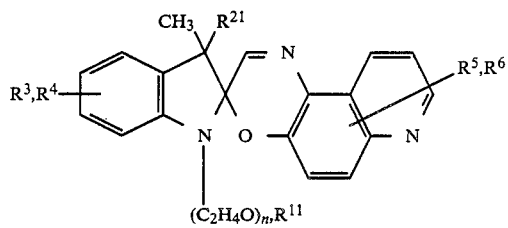 | 152 |

While the invention has been described in detail and with reference to speicific embodiments thereof, it will be apparent to one skilled in the art that various changes and modifications can be made therein without departing from the spirit and scope thereof.

What is claimed is:

1. A spiroxazine compound represented by the formula:

$$\begin{array}{c}\text{CH}_3 \quad R^2 \\ A \quad \diagdown \diagup \quad N \\ \diagup \quad \diagdown \quad B \\ N \quad X \\ | \\ (C_2H_4O)_n R^1 \end{array}$$

wherein $R^1$ and $R^2$ each represents an alkyl group, an allyl group, an aryl group or an aralkyl group; rings A and B each represents a substituted or unsubstituted benzene ring, a substituted or unsubstituted pyridine ring, or a substituted or unsubstituted pyrimidine ring; X represents an oxygen atom; and n represents an integer of from 1 to 6; and wherein the substituents for the substituted rings are one or more of the group consisting of an alkyl group, a halogen atom, an alkoxy group or an alkoxycarbonyl group.

2. A spiroxazine compound represented by the formula:

$$\begin{array}{c}\text{CH}_3 \quad R^{21} \\ R^3, R^4 \diagdown \diagup \quad N \\ \diagup \quad \diagdown \quad R^5, R^6 \\ N \quad O \\ | \\ (C_2H_4O)_{n'} R^{11} \end{array}$$

wherein $R^{11}$ and $R^{21}$ each represents an alkyl group; $R^3$, $R^4$, $R^5$ and $R^6$ each represents a hydrogen atom, a halogen atom, an alkyl group, an alkoxy group or an alkoxycarbonyl group; and n represents an integer of from 1 to 4.

3. A spiroxazine compound as in claim 2, wherein $R^{11}$ is an alkyl group having from 1 to 28 carbon atoms; $R^{21}$ is an alkyl group having from 1 to 6 carbon atoms; $R^3$, $R^4$, $R^5$ and $R^6$ each is a hydrogen atom, a halogen atom, an alkyl group having from 1 to 6 carbon atoms, an alkoxy group having from 1 to 6 carbon atoms or an alkoxycarbonyl group having from 1 to 6 carbon atoms; and n' is as defined in claim 2.

4. A spiroxazine compound as in claim 3, wherein $R^{21}$ is a methyl group; $R^3$, $R^4$, $R^5$ and $R^6$ each is a hydrogen atom, a halogen atom, an alkyl group having from 1 to 3 carbon atoms, an alkoxy group having from 1 to 3 carbon atoms or an alkoxycarbonyl group having from 1 to 3 carbon atoms; and $R^{11}$ and n' are as defined in claim 3.

5. A spiroxazine compound as in claim 4, wherein $R^3$, $R^4$, $R^5$ and $R^6$ each is a hydrogen atom, a chlorine atom, a bromine atom, an iodine atom, a methyl group, an ethyl group, a methoxy group, an ethoxy group, a methoxycarbonyl group or an ethoxycarbonyl group; and $R^{11}$ and n' are as defined in claim 4.

6. A spiroxazine compound represented by the formula:

$$\begin{array}{c}\text{CH}_3 \quad R^{21} \\ R^3, R^4 \diagdown \diagup \quad N \\ \diagup \quad \diagdown \quad R^5, R^6 \\ N \quad O \\ | \\ (C_2H_4O)_{n'} R^{11} \end{array}$$

wherein $R^{11}$ and $R^{21}$ each represents an alkyl group; $R^3$, $R^4$, $R^5$ and $R^6$ each represents a hydrogen atom, a halogen atom, an alkyl group, an alkoxy group or an alkoxycarbonyl group; and n' represents an integer of from 1 to 4.

7. A spiroxazine compound as in claim 6 wherein $R^{11}$ is an alkyl group having from 1 to 28 carbon atoms; $R^{21}$ is an alkyl group having from 1 to 6 carbon atoms; $R^3$, $R^4$, $R^5$ and $R^6$ each is a hydrogen atom, a halogen atom, an alkyl group having from 1 to 6 carbon atoms, an alkoxy group having from 1 to 6 carbon atoms or an alkoxycarbonyl group having from 1 to 6 carbon atoms; and n' is as defined in claim 6.

8. A spiroxazine compound as in claim 7, wherein $R^{21}$ is an alkyl group having from 1 to 3 carbon atoms; $R^3$, $R^4$, $R^5$ and $R^6$ each is a hydrogen atom, a halaogen atom, an alkyl group having from 1 to 3 carbon atoms, an alkoxy group having from 1 to 3 carbon atoms or an alkoxycarbonyl group having from 1 to 3 carbon atoms; and $R^{11}$ and n' are as defined in claim 7.

9. A spiroxazine compound as in claim 8, wherein $R^{21}$ is a methyl group or an ethyl group; and $R^3$, $R^4$, $R^5$, $R^6$, $R^{11}$ and n' are as defined in claim 8.

10. A spiroxazine compound as in claim 1, wherein the substituents are one or more of the group consisting of an alkyl group having from 1 to 28 carbon atoms, a hydrogen atom, a halogen atom, an alkoxy group having from 1 to 6 carbon atoms or an alkoxycarbonyl group having from 1 to 6 carbon atoms.

11. A spiroxazine compound represented by the formula:

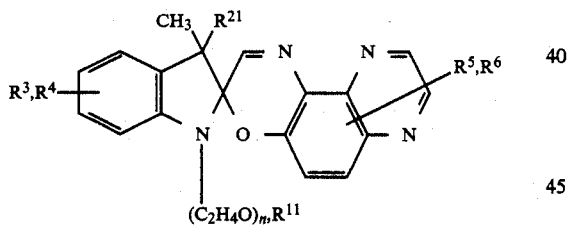

wherein $R^{11}$ and $R^{21}$ each represents an alkyl group; $R^3$, $R^4$, $R^5$ and $R^6$ each represents a hydrogen atom, a halogen atom, an alkyl group, an alkoxy group or an alkoxycarbonyl group; and n represents an integer of from 1 to 4.

12. A spiroxazine compound represented by the formula:

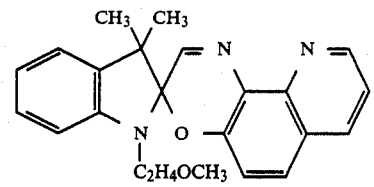

13. A spiroxazine compound as in claim 5, wherein the compound is represented by the formula:

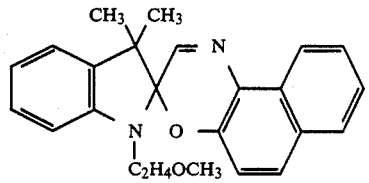

14. A spiroxazine compound as in claim 5, wherein the compound is represented by the formula:

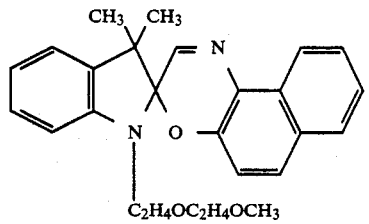

15. A spiroxazine compound as in claim 5, wherein the compound is represented by the formula:

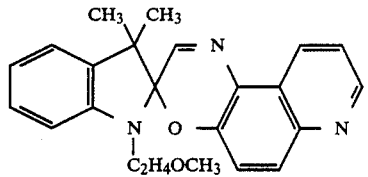

16. A spiroxazine compound as in claim 5, wherein the compound is represented by the formula:

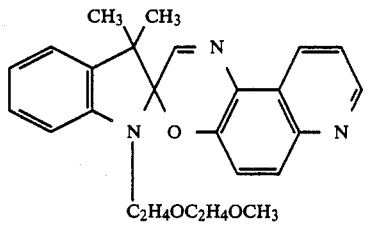

* * * * *